(12) United States Patent
Butler et al.

(10) Patent No.: US 8,502,004 B2
(45) Date of Patent: *Aug. 6, 2013

(54) PROCESS FOR EVALUATING A REFINERY FEEDSTOCK

(75) Inventors: Graham Butler, Churt (GB); John William Couves, Bourne End (GB); Paul Greenough, Beaconsfield (GB); Nicholas John Gudde, Windlesham (GB); Michael Graham Hodges, Wonersh (GB)

(73) Assignee: BP Oil International Limited, Middlesex (GB)

( * ) Notice: Subject to any disclaimer, the term of this patent is extended or adjusted under 35 U.S.C. 154(b) by 1079 days.

This patent is subject to a terminal disclaimer.

(21) Appl. No.: 11/662,893

(22) PCT Filed: Sep. 14, 2005

(86) PCT No.: PCT/GB2005/003555
§ 371 (c)(1),
(2), (4) Date: Mar. 15, 2007

(87) PCT Pub. No.: WO2006/030215
PCT Pub. Date: Mar. 23, 2006

(65) Prior Publication Data
US 2008/0102529 A1    May 1, 2008

(30) Foreign Application Priority Data

Sep. 15, 2004  (GB) .................................. 0420562.1
Sep. 15, 2004  (GB) .................................. 0420564.7

(51) Int. Cl.
*G01N 33/26* (2006.01)

(52) U.S. Cl.
USPC ........... 585/301; 700/266; 700/268; 700/271; 585/300; 585/310; 585/800; 422/68.1; 422/81; 422/83; 422/93; 422/211; 436/37; 436/55; 73/53.05; 73/61.62; 73/71.65

(58) Field of Classification Search
USPC .................. 422/68.1, 81, 82, 83, 93; 436/37, 436/55; 702/182; 73/53.05, 61.62, 71.65, 73/865.6, 866; 700/266, 271, 268; 585/300, 585/301, 310, 800

See application file for complete search history.

(56) References Cited

U.S. PATENT DOCUMENTS

| | | | |
|---|---|---|---|
| 3,960,707 A * | 6/1976 | Gross et al. .................... | 208/113 |
| 5,186,904 A | 2/1993 | Lyzinski et al. | |
| 5,600,134 A | 2/1997 | Ashe et al. | |
| 5,661,233 A | 8/1997 | Spates et al. | |
| 5,699,270 A | 12/1997 | Ashe et al. | |
| 5,817,517 A | 10/1998 | Perry et al. | |
| 5,841,678 A * | 11/1998 | Hasenberg et al. ............. | 703/10 |
| 6,159,255 A | 12/2000 | Perkins | |
| 6,339,473 B1 | 1/2002 | Gordon | |
| 6,551,832 B1 * | 4/2003 | Deves et al. .................... | 436/37 |
| 2002/0182735 A1 | 12/2002 | Kibby et al. | |
| 2003/0125884 A1 | 7/2003 | Linsen et al. | |
| 2004/0106204 A1 | 6/2004 | Chimenti et al. | |
| 2005/0019940 A1 | 1/2005 | Linsen et al. | |

FOREIGN PATENT DOCUMENTS

| | | |
|---|---|---|
| EP | 0 392 475 A2 | 10/1990 |
| EP | 0 417 305 A1 | 3/1991 |
| JP | 2004-513214 A | 4/2004 |
| WO | WO 02/36718 A1 | 5/2002 |

* cited by examiner

*Primary Examiner* — Jill Warden
*Assistant Examiner* — Shogo Sasaki
(74) *Attorney, Agent, or Firm* — Nixon & Vanderhye

(57) ABSTRACT

Process for evaluating the effect of a refinery feedstock on a refinery process by (i) providing a refinery feedstock (ii) treating the refinery feedstock to produce a plurality of fractions each representative of a feedstock for the refinery process, the plurality of fractions having at least two fractions with different properties; (iii) treating each of the plurality of fractions under experimental conditions representative of those in the refinery process, the treatments being carried out in an essentially parallel manner; and (iv) determining one or more performance criteria for each fraction for the refinery process by analyzing the respective product streams produced from each fraction at least partially in parallel.

21 Claims, No Drawings

PROCESS FOR EVALUATING A REFINERY FEEDSTOCK

This application is the U.S. National Phase of International Application PCT/GB2005/003555, filed 14 Sep. 2005, which designated the U.S. PCT/GB2005/003555 claims priority to British Application No. 0420564.7, filed 15 Sep. 2004 and British Application No. 0420562.1, filed 15 Sep. 2004. The entire content of these applications are incorporated herein by reference.

This invention relates to processes for the evaluation of the effect of refinery feedstocks on refinery processes using high throughput experimentation.

Over recent years, a number of high throughput experimentation techniques have been developed to allow significant increases in the ability to synthesize and test catalytic and other materials for useful properties. In general, such techniques have focussed on development of apparatus and methodologies, including the growing use of robots and computers to design experiments and to automate catalyst and materials preparation and testing, to allow rapid and reproducible testing results to be achieved on relatively small scale samples. For example, much effort has gone in to developing preparation and testing apparatus for numerous types of materials and material properties (such as described in U.S. Pat. No. 5,776,359) and for chemical reactions of interest (such as described in U.S. Pat. No. 5,959,297, U.S. Pat. No. 6,063,633 and U.S. Pat. No. 6,306,658).

The high throughput technologies have generally focussed on discovery of new catalysts and materials for existing processes. We have now developed high throughput methodologies that can be applied to screening and optimisation of feedstocks to refinery processes enabling optimal selection of feedstock, including feedstock blends.

Thus, according to a first aspect of the present invention there is provided a process for evaluating the effect of a refinery feedstock on a refinery process, said process comprising:
(i) providing a refinery feedstock;
(ii) treating said refinery feedstock to produce a plurality of fractions each representative of the typical feedstock for the refinery process of interest, said plurality of fractions comprising at least two fractions with different properties;
(iii) treating each of the plurality of fractions under experimental conditions representative of those in the refinery process, said treatments being carried out in an essentially parallel manner; and
(iv) determining one or more performance criteria in respect of each fraction for the refinery process.

The refinery feedstock may be any suitable refinery feedstock, including a crude oil, a synthetic crude, a biocomponent, an intermediate stream, such as a residue, gas oil, vacuum gas oil, naphtha or cracked stock, and blends of one or more of said components, such as a blend of one or more crude oils or a blend of one or more crude oils with one or more synthetic crudes.

On a typical refinery, a number of different refinery feedstocks are processed, such as a number of different crude oils. The refinery feedstocks are also usually blends of available feeds, and thus, it is very difficult to predict the effect of the feedstock on the overall refinery process, including detailed product quality and yield. Typically, a number of assumptions are made on the basis of previous operating experience, but these can usually only provide an approximate prediction. The invention enables the valuation of different feedstocks, including feedstock blends, such that these are optimised, via measured data, for the refinery processes and catalysts. The process conditions may then be further optimised to further enhance value generation. By using measured data synergist effects are captured which cannot be modelled from only limited plant data as used in conventional pilot plants and process models. The ability to map feedstock composition impact on processability and product quality enables determination of the value of a given feedstock within given blends of feedstocks. In effect, the invention permits the measurement of quality and yield of products to be linked with valuation of feedstock. Given the quality of the product, operating conditions of the processes yields of products, and know prices of the day for given quality of product and the feedstocks then the measured data can be used for a true valuation of feedstock and to impact feedstock purchase decisions, product optimisation to market requirements, and energy use minimisation. The invention allows synergistic and antagonistic effects not captured by conventional process models to be taken into consideration.

The present invention provides a process for the evaluation of the effect of a refinery feedstock on a refinery process that allows the potential value of a refinery feedstock to be evaluated prior to its use, and potentially even before its purchase. As part of this evaluation, the present invention can provide a process for the evaluation of the effect of, for example synergies obtained by, blending of said refinery feedstock with one or more other refinery feedstocks on said refinery process. Since refinery feedstocks are typically blends of two or more refinery feedstocks that are available to the refinery, this allows the effect of blending in differing ratios to be evaluated and valued, by measurement of the impact of blend composition on processing.

The present invention can also allow the overall refinery process to be optimized for the refinery feedstock, including optimization of various process parameters, and even aid selection of the most appropriate refinery at which a feedstock should be processed where more than one option is available. The present invention uses high throughput techniques, and the throughput of the overall workflow is important, with the rate of production of fractions in step (ii) preferably being at least 6, for example at least 18, at least 50, or at least 150, per week, and the number of treatments carried out in step (iii) preferably being at least 18, for example at least 54, at least 150, or at least 450, per day.

The process of the present invention may be applied to any suitable refinery processes, such as those described, for example, in Handbook of Petroleum Refining Processes ($2^{nd}$ Edition), edited by Robert A Meyers and published by McGraw-Hill.

The process of the present invention may be applied to both catalysed and uncatalysed refinery processes, and "experimental conditions", as used herein, is defined accordingly to include process conditions, such as temperature, and, where appropriate, any catalyst that may be required. Thus, when applied to a catalysed refinery process, "different sets of experimental conditions representative of those in the refinery process" may include the use of different catalysts and/or the use of different process conditions. In contrast, when applied to an uncatalysed refinery process, "different sets of experimental conditions representative of those in the refinery process" includes only the use of different process conditions.

Typical catalysed refinery processes to which the process of the present invention may be applied include hydrotreating, selective hydrotreating, isomerisation, aromatic saturation, hydroisomerisation, hydrocracking, hydrogenation, catalytic cracking, combi cracking, reforming, iso-dewaxing, sweetening (e.g. the Merox process), dealkylation, transalkylation, etherification, OATS, catalytic dehydrogenation (e.g. the Oleflex process), $C_3$ or $C_4$ olefin dimerization (e.g. the Dimersol process), MTBE, Isal, alkylation and Octgain.

Typical uncatalysed processes in a refinery include crude oil desalting, crude oil distillation, vacuum distillation, membrane extraction, solvent extraction, thermal cracking (e.g. visbreaking) and gasification.

Where the refinery process of the present invention is a catalysed refinery process, the "conditions representative of those in the refinery process" may include provision of a plurality of suitable catalysts. Typically, the plurality of suitable catalysts will comprise at least 7 such catalysts, preferably at least 20 such catalysts. Any suitable catalysts may be used. The catalysts may be "known catalysts", by which is meant, catalysts which it would be apparent to the skilled person are suitable for use in such a process, and includes catalysts which are actually in use or have been used in refineries, which are offered for use in refineries and/or which have been identified in publications as suitable for use in refineries. Typical refinery process catalysts may be described, for example, in Handbook of Petroleum Refining Processes ($2^{nd}$ Edition), edited by Robert A Meyers and published by McGraw-Hill.

The plurality of known catalysts may be provided in any suitable form. The catalysts may be solid or liquid catalysts. In one embodiment, the plurality of known catalysts may be provided as a microfabricated array of catalysts, for example on a silicon wafer. New or experimental catalysts may also be present in the plurality of catalysts, but preferably the majority (i.e. greater than 50%) of the catalysts will be "known catalysts".

In one embodiment, the plurality of catalysts may be a plurality of different catalysts chosen to cover a spectrum of known catalysts for said process, such that a number of potential catalysts may be evaluated in parallel.

In a second, alternative, embodiment the plurality of catalysts may comprise all the same catalyst or may comprise only a few different catalysts, such as only 1 catalyst or only 2 to 3 different catalysts, and the process of the present invention may be predominantly) used to evaluate the effects of differences in process conditions and/or in the properties of the fractions representative of the typical feedstock. This may be useful to enable prediction and optimisation of the performance of existing refinery process configurations at a refinery for a particular refinery feedstock, and optimisation of the feedstock, feedstock blend, or fraction blends to the refinery.

In one example of this second embodiment, suitable for an existing refinery configuration, the plurality of known catalysts may all be the same catalyst and equivalent to the catalyst currently in use in the appropriate process at the refinery. In this instance, a plurality of fractions with desired properties are treated by contacting with each of the plurality of catalysts, wherein at a particular instance, the plurality of fractions consist of fractions having a number of different properties and/or the plurality of fractions are contacted with each of the plurality of catalysts at a number of different process conditions, such as temperature. In an alternative example of this second embodiment, catalysts other than those equivalent to the catalyst currently in use at the refinery may also be present, for example for evaluation of catalysts that may be available to the refinery in the event of a catalyst change, but typically the majority of the catalysts present will be equivalent to the catalyst currently in use at the refinery.

In step (ii) of the present invention the refinery feedstock is treated to produce a plurality of fractions each representative of the typical feedstock for said refinery process of interest.

By "representative of" is meant having at least some similar chemical and/or physical properties as the typical feedstock to said refinery process.

For example, the plurality of fractions preferably have a boiling point range typical for the feedstock to the equivalent process on a refinery. A fraction with the desired boiling point range may be obtained by use of a suitable separation means, such as distillation, for example, atmospheric or vacuum distillation.

Chemical and physical properties of the feedstock to a particular catalysed refinery processes will depend on a particular refinery configuration, but typical properties are described, for example, in Handbook of Petroleum Refining Processes ($2^{nd}$ Edition), edited by Robert A Meyers and published by McGraw-Hill.

In one embodiment, the plurality of fractions may be produced by treatment of the whole of the refinery feedstock to produce a single fraction with the desired properties, which is then divided into a plurality of fractions each having the desired properties, such as the same boiling point range.

Alternatively, the refinery feedstock may be divided initially to produce 2 or more portions, and each portion is treated to produce a fraction with desired properties. These properties will be different from each other, for example, the portions may be treated to produce fractions with slightly different boiling point ranges within a total range typical for said refinery process or may be chemically treated as further described herein. For example, where a process may be operated using feedstocks with a variable boiling point range in the range of 150-250° C., a first portion may be treated to produce a fraction of boiling point range 150° C. to 250° C., and a second portion may be treated to produce a fraction of boiling point range 160° C. to 230° C.

One or more of these separate fractions may subsequently be further divided to produce the required number of fractions with the desired properties. In one extreme, the refinery feedstock may be divided to produce a portion for each of the plurality of fractions subsequently desired, wherein each portion is treated to produce a fraction with the desired properties, such as with a desired boiling point range.

In addition to, or optionally in alternative to, any other treatments of the refinery feedstock to produce a plurality of fractions each representative of the typical feedstock for said refinery process, the treating of the refinery feedstock to be evaluated may comprise the step of blending said refinery feedstock with one or more other refinery feedstocks, and, in particular, may include producing a plurality of fractions of differing properties by blending portions of the initial refinery feedstock with different other refinery feedstocks and/or with other refinery feedstocks in different ratios. Thus, in a preferred embodiment of the process of the invention, a refinery feedstock may be blended with one or more other refinery feedstocks, and the blended refinery feedstock used in the process of the invention. The blended refinery feedstock may typically comprise a blend of 3 to 20 different components, such as crude oils. It will be appreciated that a large amount of useful data can be generated by blending together a plurality of feedstocks; from the blend producing a plurality of fractions; and treating each fraction under a plurality of experimental conditions.

In general, any suitable physical or chemical treatment method may be used to obtain the fractions representative of the typical feedstock for said refinery process. For example, a microdistillation column or microfractionator may be used on each portion to obtain fractions with defined boiling point ranges. Other techniques may include solvent extraction, membrane treatments, adsorption treatments and suitable chemical reactions. Combinations of techniques may be required, for example, micro-distillation followed by a chemical reaction to represent crude oil distillation followed by a conventional treatment of said fraction that occurs before the process of interest in a refinery. For example, the feedstock to catalytic reforming process is typically hydrotreated before said reforming process.

Chemical treatment of the refinery feedstock may also comprise additive treatment, for example, addition of desalting additives, corrosion passivation additives (typically used in distillation columns), anti foulants (used in various refinery processes).

In particular, the present invention may be used to evaluate the effect of the additive treatment (different additives and/or different concentrations of additives) on the refinery feedstock in the refinery process.

The treatment in step (ii) may comprise dividing the refinery feedstock into a plurality of portions and subsequently treating each portion to produce a fraction with a boiling point range typical for a suitable fraction conventionally obtained from a crude distillation unit at a refinery. For example, the treatment in step (ii) may comprise dividing the refinery feedstock into a plurality of portions and subsequently treating each portion to produce a fraction with a boiling point range in the range of 150° C. to 250° C., which is a typical range for the kerosene fraction of crude oil, or 200° C. to 350° C., which is a typical range for the gas oil fraction of a crude oil.

It should be noted that these ranges overlap. This is one example of the usefulness of varying the boiling point range of the fractions within the overall possible range for a particular subsequent process.

The dividing may be achieved by any suitable means. For example, the dividing may be performed in a batch mode by using one or more automated syringes to provide the plurality of portions. Alternatively, a series of microflow controllers or microvalves may be used in which the flow for each portion is generally continuous, but can be started and stopped, and optionally varied, using the valve or controller. As a further alternative, a plurality of baffles or other flow control means, such as orifices in a plate, where flow can't be shut-off or Varied independently for each portion, but which provide an even flow distribution across the plurality of portions, may be used.

In one embodiment, the portion is placed on a heating device, heat is then applied to increase the sample temperature, and the fraction which boils between the desired ranges is collected, for example, by using a suitable valve to collect the fraction of the correct boiling range, which is then cooled to condense said fraction. The heating device may be a heated microoscillator, as described in U.S. Pat. No. 5,661,233.

In another embodiment, each portion may be placed in an enclosed channel comprising at least three sections, each section separated by valves or other suitable barriers which liquid samples cannot pass, but gaseous samples can. Thus, each portion may be placed in the first section of a channel and the first section heated to the upper boiling point of the boiling point range desired, for example using a heating laser to give local heating, and the second section may be maintained at ambient temperature (or below), such that all material with a boiling point below the upper boiling point vaporises and passes from the first section into the second section, where it condenses.

The second section is then heated to the lower boiling point of the range desired, for example using a heating laser to give local heating, and the third section is maintained at ambient temperature (or below), wherein all material with a boiling point below the lower boiling point vaporises and passes from the second section into the third section, leaving, in the second section, a fraction with the desired boiling point range.

Alternatively, the second section may maintained at the lower boiling point throughout, such that material with a boiling point above the range desired remains in section 1, material with a boiling point in the range desired is collected in section 2, and material with a boiling point below the range desired is collected in section 3.

A plurality of channels, each having the at least three sections may be provided on a spinning disk-type separation device as described in WO 01/87485 or WO 2004/58406. In step (iii) each of the plurality of fractions with the desired properties is treated under experimental conditions representative of those in the refinery process.

As noted above, "experimental conditions" as used herein, includes process conditions generally, and also includes the catalyst for a catalysed process. Thus, for a catalysed process "treatment" will comprise contacting each of the fractions with one of a plurality of catalysts under suitable process conditions in a suitable reactor.

In general, the treatment in step (iii) will be performed under process conditions representative of process conditions in the conventional refinery process. The process conditions in step (iii) will generally be process dependent, and, where the process is a catalysed process, may also be catalyst dependent. Process conditions may include, for example, temperature, contact time/space velocity and/or total pressure or partial pressure of specific reactants, e.g. hydrogen partial pressure is a variable in hydrotreating.

For temperature, for example, the treatments in step (iii) of each of the plurality of fractions may all be performed at the same temperature, or the treatments may be performed at different temperatures for at least some of the fractions. For a catalysed process the temperatures used for each fraction may be dependent on the catalyst present.

Similarly, the treatments in step (iii) of each of the plurality of fractions may all be performed the same space velocity, or may be performed at different space velocity for at least some of the fractions.

The temperatures and other process conditions at which the fraction is treated in step (iii) may also be varied with time to enable the optimum process conditions for each fraction in the refinery process to be determined.

The process of the present invention is performed on a small scale to enable rapid throughput and parallelisation. Typically, for a catalysed process, the volume of catalyst in each reactor is in the range of 10 µl to 10 ml, such as 10 µl to 1 ml.

Step (iv) of the present invention involves determining one or more performance criteria in respect of the feedstock for each refinery process. Suitable performance criteria may be process dependent, but may include, generally, energy efficiency, desired product yield and product quality in respect of the feedstock for each refinery process, and/or, specifically for catalysed processes, may include catalyst lifetime, catalyst activity, catalyst selectivity and catalyst (mechanical) stability.

Typically, step (iv) involves analysis of the product stream and/or, where present, the catalyst, to determine one or more of the desired parameters. The analysis may be by any suitable technique. For example, the product stream analysis may be by gas chromatography, micro gas chromatography (using a micro chip column), mass spectrometry, micro mass spectrometry, or using a spectroscopic or micro spectroscopic technique, or via micro sensors for specific physical or chemical properties, e.g. acidity, density, pour point.

It is a feature of the present invention that the effect of a refinery feedstock on a refinery process is evaluated by treating each of said plurality of fractions in an essentially parallel manner, i.e. substantially simultaneously. In general, the plurality of fractions comprises at least 7 such fractions which are treated in parallel, such as at least 20 such fractions. Where the refinery process is a catalysed process, therefore, there may be provided a corresponding number of catalyst samples.

Where the determination of performance criteria is by analysis of the product streams, then this analysis may be performed entirely sequentially using a rapid analysis tool, such as fast GC, micro GC, mass spectrometry, or micro spectroscopy, which can analyse the respective product streams one after another. Alternatively, the analysis may be performed at least partially in parallel i.e. by using two or more micro analytical devices operating on different product streams. For example, a separate analytical device, for example a micro-GC, micro spectrometer or micro sensor, may be provided for analysis of each product stream, such that all the product streams can be analysed in parallel.

Other types of parallel analysis that may be used include plate-based liquid chromatography, plate-based electrophoresis, and/or multi sensor arrays, where multiple samples can be analysed in parallel on a single plate.

In addition to any analysis of the product stream that may be performed in step (iv) of the process of the present invention, analysis to determine chemical and/or physical properties may be performed on any suitable streams in the process of the present invention. For example, in one embodiment, the fractions obtained from the treatment step (ii) of the process of the present invention may be subject to analysis to determine one or more chemical or physical properties of said streams before they are treated in step (iii). Such properties, the desired ones of which may be stream dependent, may include density, specific gravity, total acid number (TAN), total base number (TBN), cold flow properties (such as pour point, freezing point and cloud point), viscosity, hydrocarbon speciation (e.g. aromatics content), sulphur content, nitrogen content, nickel content, vanadium content and combinations thereof. Any suitable analytical technique may be used, including spectroscopic, chromatographic and electrophoretic techniques, or specific property sensor techniques, previously described as suitable for analysis of the product stream from step (iii).

In the process of the present invention, the evaluation of the effect of a refinery feedstock on a refinery process requires that the plurality of fractions comprise at least two fractions with different properties. Typically, the majority of the fractions are treated in a differing manner, by which is meant that the properties of the fraction and/or the experimental conditions are different for at least 50%, preferably at least 80%, of the plurality of fractions tested. Some "identical" experiments may be performed for the purposes of ensuring reproducibility. Preferably, in the process of the present invention the plurality of fractions comprise at least four fractions with different properties, such as at least eight fractions with different properties.

The evaluation according to the process of the present invention may be enhanced by performing further experiments repeating steps (ii) to (iv) of the present invention. Thus, whilst the effect of a refinery feedstock on a refinery process may be evaluated for a plurality of different experimental conditions, such as a plurality of different catalysts, by taking a fraction with one boiling range in step (ii), the overall evaluation may be enhanced by repeating steps (ii) to (iv) for a fraction of the same initial feedstock but which has been treated in a slightly different manner, for example, such that is has a different boiling point range within an overall boiling point range representative of that typical for a fraction conventionally obtainable for said process at a refinery.

Since refineries do have the ability to vary the operation, such as of a distillation column, within certain ranges to select different temperature ranges for particular cuts of a feedstock, this can enable the process of the present invention to provide information on the optimum operating conditions for the distillation column in a refinery as well as identifying the optimum catalyst and process conditions for subsequent reaction of said cut.

Preferably, the process of the present invention is performed in a continuous manner, by which is meant that the treatment to produce a plurality of fractions each representative of the typical feedstock for said refinery process in step (ii) and the treatment of said fractions in step (iii) is performed in an integrated and continuous, rather than a batch-type, manner. Thus, the treatment of step (ii) may comprise continuously feeding the refinery feedstock to treatment steps to produce a plurality of fractions as streams which are subsequently treated in a flow-through manner in step (iii). This represents the processes generally occurring in a refinery more closely, and is different to typical crude oil assay testing, which is generally performed in batch tests. By operating in a continuous manner a more rapid analysis may be achieved, since it is not necessary for a large sample (batch) of a particular fraction to be obtained from the treatment step (ii) before it is subsequently fed to step (iii).

When the invention is performed in a continuous manner it is also possible to vary certain properties of the plurality of fractions in a continuous or semi-continuous manner, for example, to explore the effect of different blending ratios or fractionation temperature ranges and/or to vary the contacting conditions, such as temperature in step (iii).

The process of the present invention can be repeated as necessary for different refinery feedstocks and blends thereof.

For catalysed processes, the process of the present invention can be repeated with one or more further sets (arrays) of pluralities of catalysts for said refinery process. An array typically is a substrate having a set of regions in which materials may reside. A substrate refers to a substance having a rigid or semi-rigid surface, which, in many embodiments, at least one surface of the substrate will be substantially flat having a desired number of physically separate regions for different materials. Examples of substrates with, for example, dimples, wells, raised regions, etched trenches, etc, include microtitre plates or glass vial lined microtitre plates. In some embodiments, the substrate itself contains wells, raised regions, etched trenches, etc. which form all or part of the regions.

The process of the present invention can be applied separately to a number of different refinery processes. Thus, it is may be appropriate to have one or more arrays of suitable catalysts for evaluating hydrotreating processes on a refinery feedstock, one or more arrays of suitable catalysts for evaluating catalytic cracking processes on said refinery feedstock, and so on as required.

Alternatively, evaluation of processes may be "linked". Thus, in a further embodiment, the process of the present invention may be applied to evaluating the effect of a refinery feedstock on two or more refinery processes simultaneously. The second process may also be catalysed or uncatalysed.

In one aspect of this embodiment, the refinery feedstock may be treated to produce a plurality of fractions each representative of the typical feedstock for a first refinery process and a plurality of fractions representative of the typical feedstock for a second refinery process, and treating the respective pluralities of fractions under experimental conditions representative of the respective refinery processes. An example of this aspect includes separating a refinery feedstock into a first plurality of fractions representative of kerosene fractions from a crude distillation unit and a second plurality of fractions representative of gas oil fractions from a crude distillation unit, and passing these to respective subsequent steps.

In a second aspect of this embodiment of the present invention, the refinery feedstock may be evaluated against processes that are operated "in series" on a refinery. A typical example of two processes in series, and where both processes are catalysed, is hydrotreating of a naphtha fraction and subsequent catalytic reforming, wherein each of the plurality of fractions may be passed to a known hydrotreating catalyst and then to a known catalytic reforming catalyst.

A combination of these first and second aspects may be used to evaluate a number of processes on a refinery simultaneously. This embodiment has the advantage that the effect of a change in one factor, such as the properties of one fraction on a first process, can be simultaneously evaluated against consequent changes in other processes that are the result of this first change.

A significant number, such as at least 5 refinery processes, for example 10 or more refinery processes, may be evaluated in this "linked" way to provide information on the optimum refinery configuration for a particular feedstock. This may be achieved by providing any required catalysts and respective processing steps on a suitable microfabricated array or arrays.

Thus, a particular advantage of the present invention is that it enables fractionation and two or more different processes to be integrated in continuous manner to simulate a real refinery. Such arrays of processes and fractionation can be configured to simulate a specific refinery where the values of different feedstocks, including feedstock blends, can be valued against the specific processes and catalysts present in that refinery, and optimum process operation conditions established within the operating envelopes of all the processes such that value generated is maximised. Alternatively, the array of fractionation and processes can be configured to represent different refineries at which a feedstock might be processed such that the optimal refinery which generates the maximum value is used to process the feed.

The process of the present invention will generate a large amount of data on the effect of refinery feedstocks in refinery processes. In a further embodiment, this data may be utilised to develop, update and/or verify process models for one or more refinery processes (either individually or "linked" processes).

In addition, modelling or other experimental design techniques may be used to generate a set of variable process conditions for one or more refinery feedstocks (including blends) which it is desired to evaluate for the development, updating or verification of one or more process models, and the process of the present invention can be specifically used to evaluate the processes to generate the required data for the process models, such as yield and quality of products from the refinery feedstock or feedstocks under the defined process conditions.

The invention claimed is:

1. A process for evaluating the effect of a refinery feedstock on a refinery process, said process for evaluating comprising:
   (i) providing a refinery feedstock;
   (ii) treating said refinery feedstock to produce a plurality of fractions each representative of a feedstock for the refinery process, said plurality of fractions comprising at least two fractions with different properties, wherein the treating of said refinery feedstock is performed using a microdistillation column or microfractionator to obtain fractions with defined boiling point ranges;
   (iii) treating each of the plurality of fractions under experimental conditions representative of those in the refinery process, said treatments being carried out in an essentially parallel manner; and
   (iv) determining one or more performance criteria for each fraction for the refinery process by analysing at least partially in parallel the respective product streams produced from each fraction.

2. A process as claimed in claim 1, wherein the refinery feedstock is a crude oil, a synthetic crude, a biocomponent, an intermediate stream, or a blend of said components.

3. A process as claimed in either claim 1, wherein the plurality of fractions comprises at least 7 such fractions.

4. A process as claimed in claim 1, wherein the refinery process is an uncatalysed refinery process selected from crude oil desalting, crude oil distillation, vacuum distillation, membrane extraction, solvent extraction, thermal cracking and gasification; or a catalysed refinery process selected from hydrotreating, selective hydrotreating, isomerisation, aromatic saturation, hydroisomerisation, hydrocracking, hydrogenation, catalytic cracking, combi cracking, reforming, isodewaxing, sweetening, dealkylation, transalkylation, etherification, OATS, catalytic dehydrogenation, $C_3$ or $C_4$ olefin dimerization, MTBE, Isal, alkylation and Octgain.

5. A process as claimed in claim 1, wherein the refinery process is a catalysed process and there is provided in step (iii) a plurality of different catalysts chosen to cover a spectrum of known catalysts for said refinery process.

6. A process as claimed in claim 1, wherein the refinery process is a catalysed process and there is provided in step (iii) a plurality of catalysts which plurality of catalysts comprise all the same catalyst.

7. A process as claimed in claim 5, wherein there is provided in step (iii) at least 7 catalysts.

8. A process as claimed in claim 6, wherein there is provided in step (iii) at least 20 catalysts.

9. A process as claimed in claim 1 wherein in step (ii) the plurality of fractions are produced by treatment of the whole of the refinery feedstock to produce a single fraction with desired properties, which is then divided into a plurality of fractions each having desired properties.

10. A process as claimed in claim 1, wherein the refinery feedstock is divided initially to produce 2 or more portions, and each portion is treated to produce a fraction with desired properties.

11. A process as claimed in claim 10, wherein the treating of the refinery feedstock to be evaluated in step (ii) includes producing a plurality of fractions of differing properties by blending portions of the initial refinery feedstock with different other refinery feedstocks and/or with other refinery feedstocks in different ratios.

12. A process as claimed in claim 1 wherein the treating of the refinery feedstock comprises heating using a heated microoscillator.

13. A process as claimed in claim 1 wherein the treating in step (iii) is performed at conditions representative of conditions in the conventional refinery process.

14. A process as claimed in claim 1, wherein step (iv) of the present invention involves determining one or more performance criteria selected from catalyst lifetime, catalyst activity, catalyst selectivity, catalyst stability, energy efficiency, desired product yield and product quality for the feedstock for each refinery process.

15. A process as claimed in claim 1, wherein the evaluation of the effect of a refinery feedstock on a refinery process includes varying the properties of the plurality of fractions produced in step (ii) and/or the process conditions in step (iii).

16. A process as claimed in claim 1 which is performed in a continuous manner.

17. A process as claimed in claim 1 wherein the process is applied to evaluating the effect of a refinery feedstock on two or more refinery processes simultaneously.

18. A process as claimed in claim 17, wherein the refinery feedstock is evaluated against processes that are operated in series on a refinery.

19. A process as claimed in claim 2, wherein the refinery feedstock is a residue, gas oil, vacuum gas oil, naphtha or cracked stock.

20. A process as claimed in claim 4, wherein the thermal cracking is visbreaking.

21. A process as claimed in claim 15, wherein the evaluation of the effect of a refinery feedstock on a refinery process includes varying the boiling point range of the plurality of fractions produced in step (ii).

* * * * *